United States Patent
Baumgart

(10) Patent No.: US 7,609,814 B2
(45) Date of Patent: Oct. 27, 2009

(54) ADAPTIVE MEDICAL IMAGE AND MASK DATA PROCESSING SYSTEM

(75) Inventor: John Baumgart, Hoffman Estates, IL (US)

(73) Assignee: Siemens Medical Solutions USA, Inc., Malvern, PA (US)

(*) Notice: Subject to any disclaimer, the term of this patent is extended or adjusted under 35 U.S.C. 154(b) by 0 days.

(21) Appl. No.: 12/266,961

(22) Filed: Nov. 7, 2008

(65) Prior Publication Data

US 2009/0180591 A1 Jul. 16, 2009

Related U.S. Application Data

(60) Provisional application No. 61/021,456, filed on Jan. 16, 2008, provisional application No. 61/021,105, filed on Jan. 15, 2008.

(51) Int. Cl.
*H05G 1/64* (2006.01)
(52) U.S. Cl. ...................... 378/98.12; 378/62
(58) Field of Classification Search ............... 378/98.2, 378/98.5, 98.11, 98.12, 62, 42, 205, 206
See application file for complete search history.

(56) References Cited

U.S. PATENT DOCUMENTS

| | | | |
|---|---|---|---|
| 2004/0071265 A1* | 4/2004 | Maschke | 378/98.11 |
| 2007/0036266 A1 | 2/2007 | Kramp et al. | |
| 2008/0025586 A1 | 1/2008 | Baumgart et al. | |
| 2008/0027316 A1 | 1/2008 | Baumgart | |
| 2008/0037844 A1 | 2/2008 | Baumgart | |
| 2008/0074511 A1 | 3/2008 | Kramp et al. | |
| 2008/0101670 A1* | 5/2008 | Baumgart et al. | 382/128 |

* cited by examiner

*Primary Examiner*—Hoon Song
(74) *Attorney, Agent, or Firm*—Alexander J. Burke

(57) ABSTRACT

A system and method are disclosed for allowing the user to change the patient table position or x-ray detector position during an angiographic roadmapping procedure while still displaying a properly registered roadmap display by adapting the mask image to the new position. A system and method are further disclosed for allowing the user to change the field of view size (i.e., zoom factor) of the x-ray detector during an angiographic roadmapping procedure by matching the size of the existing mask to the live image.

42 Claims, 9 Drawing Sheets

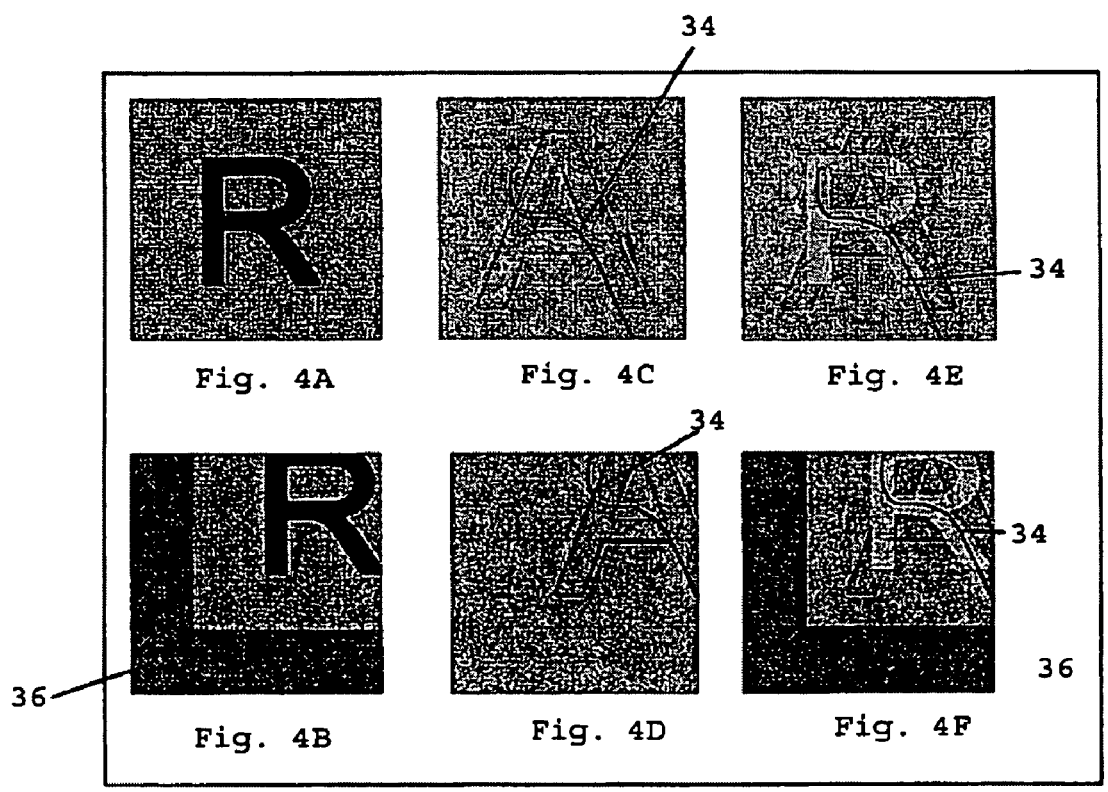

ADAPTIVE MEDICAL IMAGE AND MASK DATA PROCESSING SYSTEM

CROSS-REFERENCE TO RELATED APPLICATIONS

This is a non-provisional application of pending U.S. provisional patent application Ser. No. 61/021,456, filed Jan. 16, 2008 by John Baumgart, and is also a non-provisional of pending U.S. provisional patent application Ser. No. 61/021,105, filed Jan. 15, 2008 by John Baumgart.

FIELD OF THE DISCLOSURE

The disclosure is related to angiographic roadmapping procedures in general, and more particularly to procedures for allowing the repositioning of a patient table and/or x-ray detector or modifying the field of view of an x-ray detector during an angiographic roadmapping procedure without the need to construct a new roadmap mask.

BACKGROUND

Angiographic roadmapping is a technique commonly used for catheter navigation in endovascular procedures performed through a small puncture wound or incision often in the groin. Blockages in the arteries or veins can be treated with balloon angioplasty or the placement of stents, all through this small puncture wound.

Roadmapping consists of superimposing a live fluoroscopic image on a previously stored digitally subtracted angiogram. The digitally subtracted angiogram is generated by computer techniques which compare an x-ray image of a region of the body before and after a contrast agent has been injected intravenously into the body. Tissues and blood vessels on the first image are digitally subtracted from the second image, leaving a clear picture of the artery which can then be studied independently and in isolation from the rest of the body.

An angiographic roadmapping procedure typically consists of three phases. In the first phase, a user acquires fluoroscopic images of the region of the patient's anatomy in which an endovascular procedure will be performed. Once the x-ray has been regulated, the system switches to the second phase, in which the user injects a contrast medium into the patient's blood stream to build an opacified roadmap of the vessels using a digital subtraction technique as previously described. In the third phase, the opacified roadmap is combined with a live fluoroscopic image of the relevant region of the patient's anatomy to allow a physician guiding a catheter to see the vasculature during catheter positioning, thus eliminating the need for injecting further contrast medium.

One problem with this technique is that if the physician decides to move the patient table or x-ray detector, the roadmap will no longer be registered with the live fluoroscopic images. This can produce gross motion artifacts that make the resulting display unusable. As a result, the roadmapping procedure needs to be restarted, which results in additional time for the procedure, and often requires a new contrast injection for the patient.

Further, if the physician wishes to change the field of view of the x-ray detector during the roadmapping procedure, doing so may require the current mask to be discarded, and a new roadmap mask to be built. This too results in additional time for the physician to perform the procedure and, again, use of an additional contrast injection for the patient.

Thus, there is a need for an improved method for angiographic roadmapping that enables a physician greater flexibility in performing catheter-based procedures. Such a method should enable a physician to reposition a patient table and/or x-ray detector, or to modify the field of view of the x-ray detector during the roadmapping procedure without requiring a new roadmap mask to be constructed.

SUMMARY OF THE DISCLOSURE

A method is disclosed for adjusting an angiographic roadmapping mask. The method may comprise: (a) obtaining an original roadmapping mask of a targeted patient tissue region, (b) obtaining a live fluoroscopic image of at least a portion of the targeted patient tissue region using an x-ray source and an x-ray detector, (c) adjusting the roadmapping mask to match the live fluoroscopic image; and (d) combining the adjusted roadmapping mask and the live fluoroscopic image to provide a displayed superimposed image to a user.

A system for adjusting an angiographic roadmapping mask is also disclosed. The system may comprise an x-ray source, an x-ray detector, a patient table, a display; and a machine-readable storage medium encoded with a computer program code such that, when the computer program code is executed by a processor, the processor performs a method comprising: (a) obtaining an original roadmapping mask of a targeted patient tissue region using the x-ray source and the x-ray detector; (b) obtaining a live fluoroscopic image of at least a portion of the targeted patient tissue region using the x-ray source and the x-ray detector; (c) sensing at least one of: a position change of a patient table, a change in a distance between the x-ray source and the x-ray detector, and a change in a field of view of the x-ray detector; (d) adjusting the original roadmapping mask to match a portion of the live fluoroscopic image; (e) combining the adjusted roadmapping mask and the live fluoroscopic image to provide a superimposed image; and (f) displaying the superimposed image to a user via the display.

BRIEF DESCRIPTION OF THE DRAWINGS

The accompanying drawings illustrate preferred embodiments of the disclosed method so far devised for the practical application of the principles thereof, and in which:

FIGS. 4A-4F illustrate the steps of adapting a roadmap mask to accommodate a new table position;

DETAILED DESCRIPTION

Definitions

An angiogram uses a radiopaque substance (i.e., a contrast agent) to make blood vessels visible under x-ray. A roadmapping mask is a digitally subtracted angiogram generated by computer techniques which compare an x-ray image of a region of the body before and after a contrast agent has been injected intravenously into the body. A fluoroscopic image is an x-ray image showing internal tissues of a region of the body. A live fluoroscopic image is an x-ray image showing live movement of internal tissues of a region of the body. An original roadmapping mask is a baseline digitally subtracted angiogram. An adjusted roadmapping mask is a digitally subtracted angiogram that has been digitally altered to change one or more of the following characteristics: (a) the mask position along the x and/or y axis, (b) the mask's overall size, or (c) the mask resolution. A superimposed image is an image in which an original or adjusted roadmapping mask is combined with a live fluoroscopic image. A padded pixel is a pixel that is set to a predetermined intensity to minimize subtraction artifacts in areas of the live image for which no roadmap mask was acquired. A padded roadmapping mask is a roadmapping mask in which at least some pixels of the mask have been padded.

"Combining" a roadmap mask with live fluoroscopy is a well-known technique. In the present disclosure, this "combining" is achieved by digitally subtracting the adjusted mask in real time from the live fluoroscopic image. Since the mask contains a representation of the contrast media (i.e., the blood vessels) and the live fluoroscopic image does not, the contrast media shows up as white while the guide wire, catheter, or other medical device being guided under fluoroscopy shows up as a dark image on top of the white vessels. It will be appreciated that other techniques for combining a roadmapping mask and a live fluoroscopic image may be used to achieve a similar image. For example, a vessel map may be extracted from the roadmapping mask and then superimposed over a live fluoroscopic image.

Figure 1:
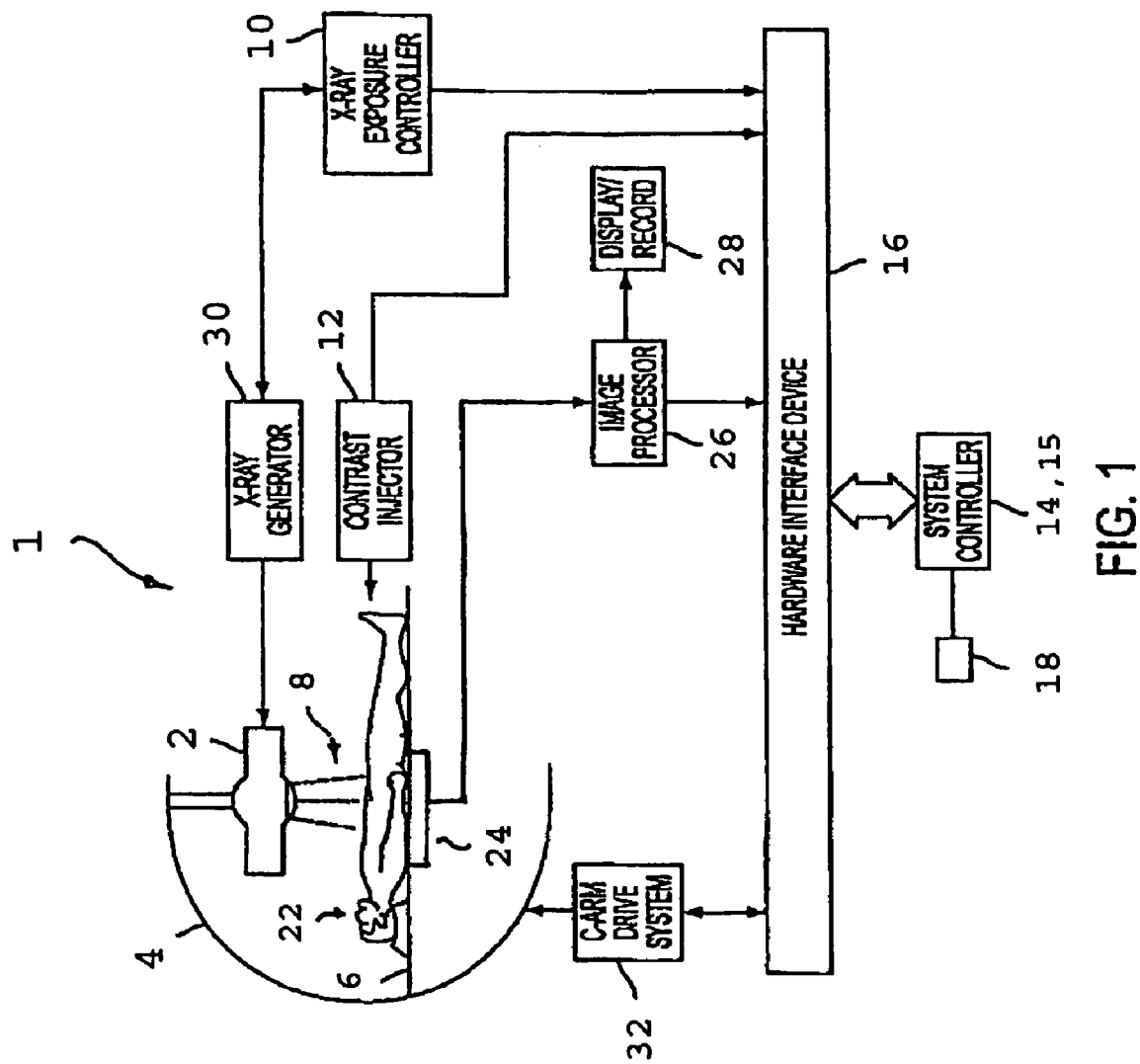
FIG. 1 is a schematic diagram showing an X-ray imaging system for performing live fluoroscopic roadmapping.

Referring to FIG. 1, an exemplary X-ray system 1 is shown for performing live fluoroscopic roadmapping. They X-ray system 1 comprises an x-ray tube or source 2 and associated support and filtering components. The X-ray source may be affixed to a support, such as a C-arm fluoroscope stand 4, or examination table 6, which would allow the X-ray source to be moved within a constrained region. The constrained region may be arcuate or otherwise three dimensional, depending on the nature of the support structure. A collimator may also be included, which will define the size and shape of X-ray beam 8 emerging from the source.

An X-ray exposure controller 10, contrast medium injector 12 and system controller 14 may also be included. System controller 14 may be a personal computer or any known controller capable of receiving and transmitting control signals to/from the above-described X-ray system components via a hardware interface 16. System controller 14 may include a user input device 18, such as a trackball, mouse, joystick, and/or computer keyboard to provide for user input in carrying out various system functions, such as mode selection, linearity control, X-ray dose control, data storage, etc. The system controller 14 may include a processor 15 executing instructions for performing one or more steps of the disclosed process.

The positions of the movable components of the system (e.g., x-ray source 2, C-arm 4, patient table 6, x-ray detector 24), may be determined using the individual motor controllers associated with the equipment. When the system 1 is initially set up, the relative positions of the movable components are calibrated so that the positions programmed into the motor controllers enable the accurate positioning of the components relative to one another.

In the illustrated embodiment, a patient 22 is shown supported on patient-support table 6 so that the generated X-ray beam 8 passes through him/her onto a detector 24, located on the patient support table 6 opposite the X-ray source. In one embodiment the detector 24 is a flat panel detector that acquires digital image frames directly, which are then transferred to an image processor 26. A display/record device 28 records and/displays the processed image(s), e.g., subtracted angiography images. The display/record device 28 may include a display for displaying the displayed image output, as well as a separate device for archiving. The image is arranged for storage in such an archive such as a network storage device.

The X-ray source 2 is controlled by the system controller 14 via exposure controller 10 and X-ray generator 30. The position of the X-ray source 2 may be adjusted via a C-arm drive system.

In a first embodiment, the system 1 may operate to compensate for movement of the patient table 6. As will be appreciated, such table movement may be required to reposition the patient with respect to the X-ray source to enable the practitioner to focus in on a particular region of the patient's anatomy.

When the table is moved, the system 1 determines the change in table location (along 3-axes) via the relative movement and/or position(s) of the associated motor controller(s). The system 1 then translates this movement (in millimeters (mm)) of the table into a corresponding pixel movement of the roadmapping mask.

As an initial step, the system 1 acquires the geometric layout of the lab components, including the distance between the x-ray source 2 and x-ray detector 24, the distance between the source and the patient 22, and the distance between the patient table 6 and the detector. This can be done in an automatic system initialization step (using information obtained from the motor controllers or other position sensors), or the values may be manually input. Based on the relative positioning of the system components, the system 1 then computes the absolute size of a pixel (in millimeters) of the image registered by the x-ray detector 24 to provide a conversion factor. Thereafter, each time a movement of the patient table 6 is registered (again, by movement of one or more of the motor controllers), the system 1, converts the absolute table movement into a pixel movement of the roadmapping mask. The roadmapping mask is then panned or translated by the number of pixels that correspond to the registered table movement. A new value of pixel size (in millimeters) is then calculated based on the new position of the patient table, and this new conversion value is used in the manner previously indicated to translate the roadmapping mask if any further changes in patient table position are sensed.

Similarly, if there is motion of the C-arm along the table, then the mask would be translated in the opposite direction of the C-arm motion using a process identical to that described in relation to the table movement.

Any pixels that are undefined as a result of this translation will be set to a 50% grey value to minimize subtraction artifacts in areas of the live image for which no roadmap mask was acquired. 50% grey represents a "perfect" subtraction (sometimes referred to as "subtraction zero"—the value of two identical pixels subtracted from each other), that blends in with the background of the subtraction performed in the defined portion of the image area (i.e., it provides a neutral background). It will be appreciated that the 50% value is not critical, however, and thus it is possible that during calculation of the subtraction and before visualization, something other than 50% grey will be used to represent "subtraction zero." It is also possible that the background will be displayed as something other than 50% grey.

In a second embodiment, the system 1 may accommodate changes in the distance between the x-ray source 2 and the x-ray detector 24 (often referred to as source-to-image distance, or SID). In this embodiment, the original roadmap mask is scaled up or down to match the pixel size of the live fluoroscopic images.

As discussed in relation to the previous embodiment, the system 1 may initially compute the size of a pixel (e.g., # pixels/millimeter) of an image registered by the x-ray detector 24. Thereafter, when the system registers a change in distance between the x-ray source 2 and the patient 22 or between the x-ray source 2 and x-ray detector 24 (using information received from the associated motor controller(s)), the system 1 registers this movement and resizes the roadmapping mask based on the change in distance. This resizing is automatically achieved through the use of a calculated conversion factor.

With the system arrangement of FIG. 1, the divergence of the x-ray beam emerging from the x-ray source 2 means that a known "similar triangles" technique may be used to convert a change in distance between the source 2 and detector 24 to a change in the size of the roadmapping mask. Since the size of the x-ray detector 24 (i.e., total number of pixels) and the initial distances between the x-ray source 2, patient 22 and x-ray detector 24, are "known," an original triangulation can be calculated. Thereafter, as the patient 22 or x-ray detector 24 are move toward or away from the source 2, a "similar triangle" conversion is performed to convert that distance change into a discrete change in the pixel size of the roadmapping mask. This conversion may be performed each time the system 1 senses a change in the distance between the x-ray source 2 and the patient 22 or x-ray detector 24.

If the SID increases, the roadmap mask will be enlarged and then cropped to match the size of the live images. If the SID decreases, the roadmap mask will be reduced and the perimeter "padded" to match the size of the live images. The padding pixels will be set to a value of 50% grey to minimize subtraction artifacts in areas of the live image for which no roadmap mask was acquired.

Fine errors in roadmap registration may be corrected using existing motion correction techniques, such as rigid image registration.

In the following descriptions, images representing a roadmap mask are represented with the letter "R" while images containing background anatomy are represented with the letter "A".

Figure 2A:
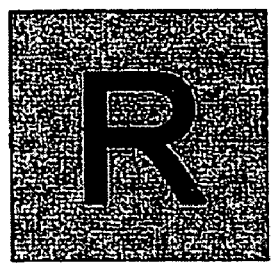
FIGS. 2A-2E illustrate steps of a traditional roadmapping procedure.
Figure 2B:
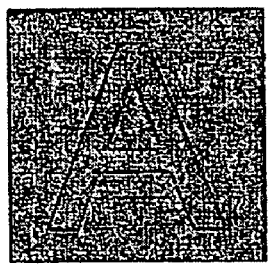
Figure 2D:
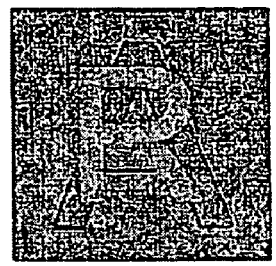
Figure 2C:
Figure 2E:
Figure 3A:
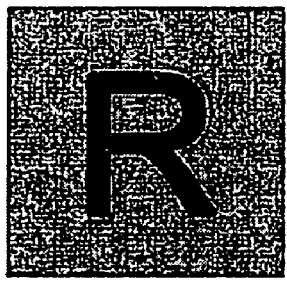
FIG. 3A-3D illustrate the steps of adapting a roadmap mask to accommodate a source-to-image-distance (SID) change.
Figure 3B:
Figure 3C:
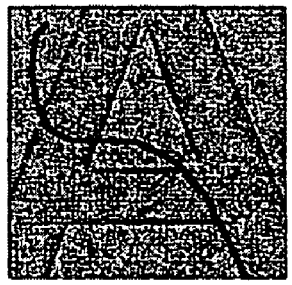
Figure 3D:

FIGS. 2A-2E illustrate the image progression in a traditional roadmapping procedure. The left column (FIG. 2A) contains the roadmap mask that will be used throughout the procedure. The center column (FIGS. 2B, 2C) represents live fluoroscopic images taken at different points in time. The top image (FIG. 2B) represents only the patient's anatomy, while the bottom image (FIG. 2C) represents the patient's anatomy with the addition of a guide wire or catheter 34 inserted. The right column (FIGS. 2D, 2E) represents the roadmap image combined with the live fluoroscopic image as seen by a user, in which the roadmap is used to assist with placement of the guide wire or catheter (FIG. 2E).

FIG. 3 illustrates a roadmap mask in which the source-to-image distance (SID) is increased (FIGS. 3A, 3B) during a medical procedure. In this example, the original roadmap mask (FIG. 3A) is enlarged (FIG. 3B) to correspond to the pixel size given by the new SID, before being combined with the anatomic image (FIG. 3C) to create the roadmapping image seen by the user (FIG. 3D).

FIG. 4 illustrates a roadmap mask in which the table is repositioned during a medical procedure. Here the original roadmap mask (FIG. 4A) is panned (FIG. 4B) according to the new position of the patient table 6 before being combined with the anatomic image (FIGS. 4C, 4D) to create the roadmapping image (FIG. 4E, 4F) seen by the user. As previously noted, pixels outside of the existing roadmap mask (region 36 of FIGS. 4B, 4F) are set to 50% gray to minimize subtraction artifacts in the corresponding portion of the displayed image.

In a third embodiment, the system may operate to adapt the size of the roadmap mask being used to the current field of view of the detector 24. When the field of view is decreased, (e.g., when the practitioner adjusts the system to obtain a closer look at the anatomy of interest during a procedure), the zoom factor increases. In such a case, the roadmap mask "R" will be scaled up (i.e., enlarged) and/or cropped to match both the resolution and size of the live fluoroscopic images. When the field of view is increased, the zoom factor decreases. In this case, the roadmap mask used will be scaled down and the image padded to match both the resolution and size of the live fluoroscopic images.

The system 1 performs this scaling up or scaling down using the following parameters: (1) the field of view of the detector (measured in pixels), and (2) the pixel size of the detector (measured in mm). Thus, for a selected change in the field of view of the x-ray detector 24, the system automatically senses this change and then changes the scale (i.e., number of pixels/mm) of the roadmapping mask by an identical amount so that the resized view of the live fluoroscopic image is matched by a correspondingly resized view of the roadmapping mask.

If it is necessary to pad the mask, pixels with a value of 50% grey will be used to minimize subtraction artifacts in areas of the live image for which no roadmap mask was acquired.

Figure 5A:
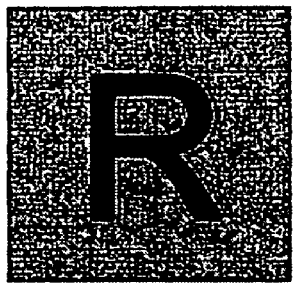
FIGS. 5A-5D illustrate the steps of adapting a roadmap mask to accommodate a change in a detector field of view.
Figure 5B:
Figure 5C:
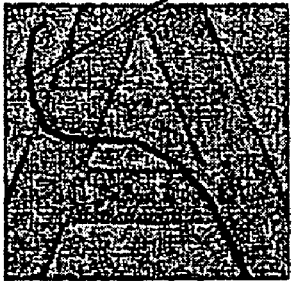
Figure 5D:
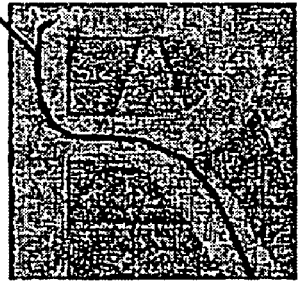

FIGS. 5A-5D illustrate this embodiment in which the field of view of the detector 24 is changed during a roadmapping procedure. The original roadmap mask (FIG. 5A) is adapted to the new field of view of the detector (FIG. 5B) before being combined with the anatomic image (FIG. 5C) to create the roadmapping image (FIG. 5D) seen by the user. This roadmapping image of FIG. 5D is then used to enable placement of the guidewire 34.

The disclosed method may provide a user with a more efficient procedure for performing angiographic roadmapping that will reduce the overall time required for the procedure, thus reducing overall radiation exposure to the patient and practitioner.

Referring now to FIGS. 6A-6D, the disclosed process may comprise the following steps. An original roadmapping mask of a targeted patient tissue region is obtained at step 100. At step 200, a live fluoroscopic image of the targeted patient tissue region is obtained. At step 300, a change is detected in at least one parameter of the system, such as a position change in the patient table 6, a change in distance between the x-ray source 2 and the x-ray detector 24, or a change in the field of view of the x-ray detector 24. The original roadmapping mask is then adjusted at step 400 to match the live fluoroscopic image based on the detected change. At step 500, the adjusted roadmapping mask is combined with the live fluoroscopic image to obtain a superimposed image that is displayed to a user at step 600.

Figure 6A:
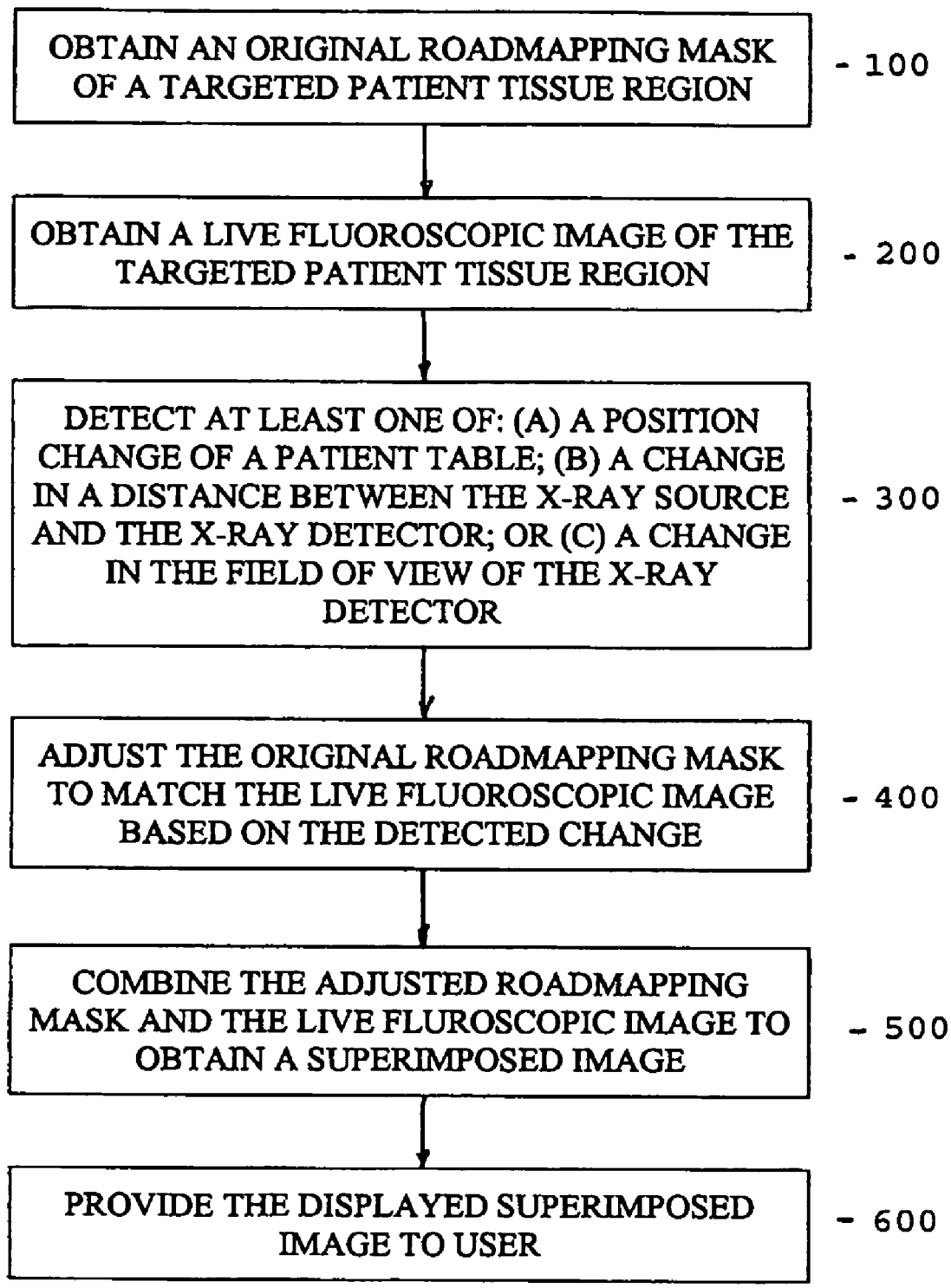
FIGS. 6A-6D show flow charts of the process performed by the disclosed system.
Figure 6B:
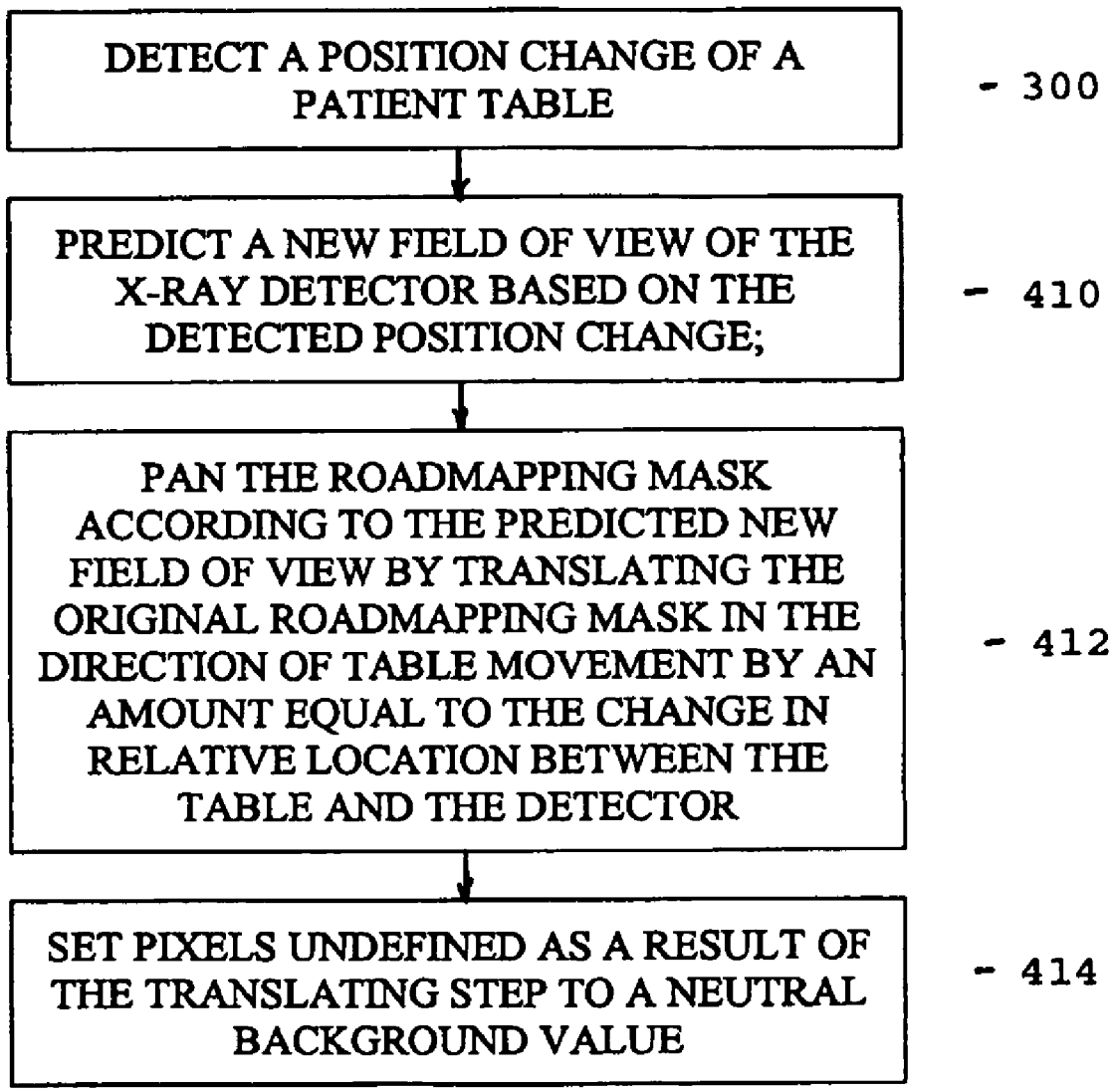
Figure 6C:
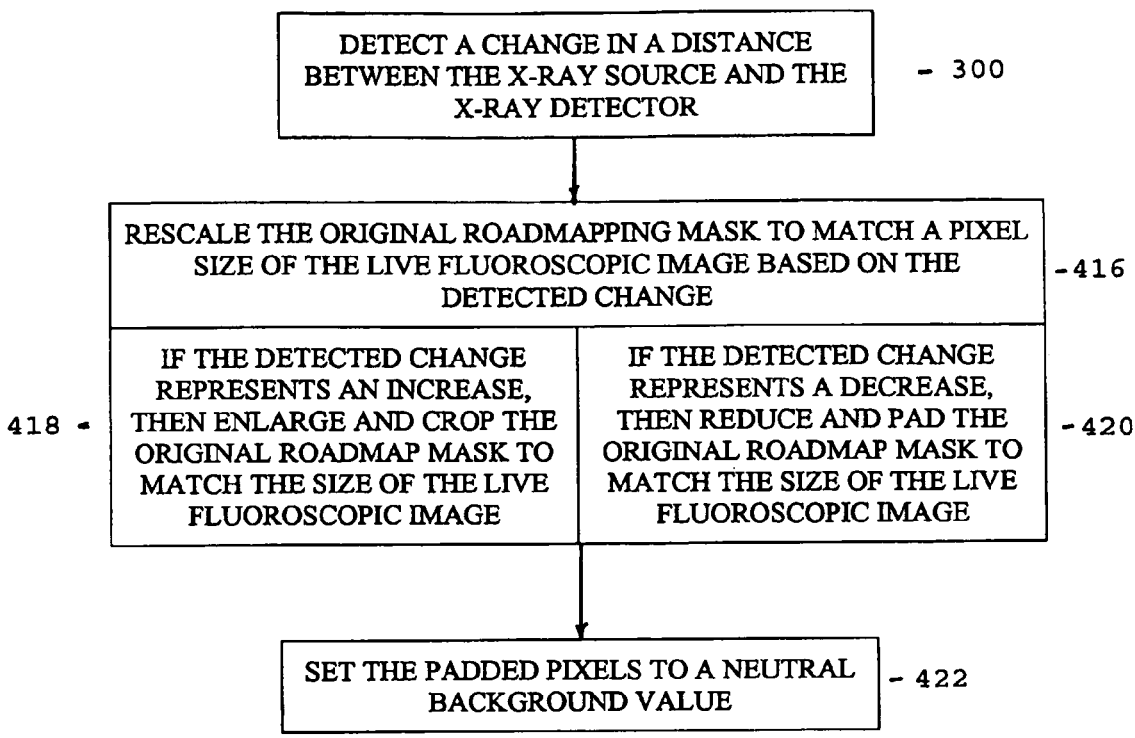
Figure 6D:
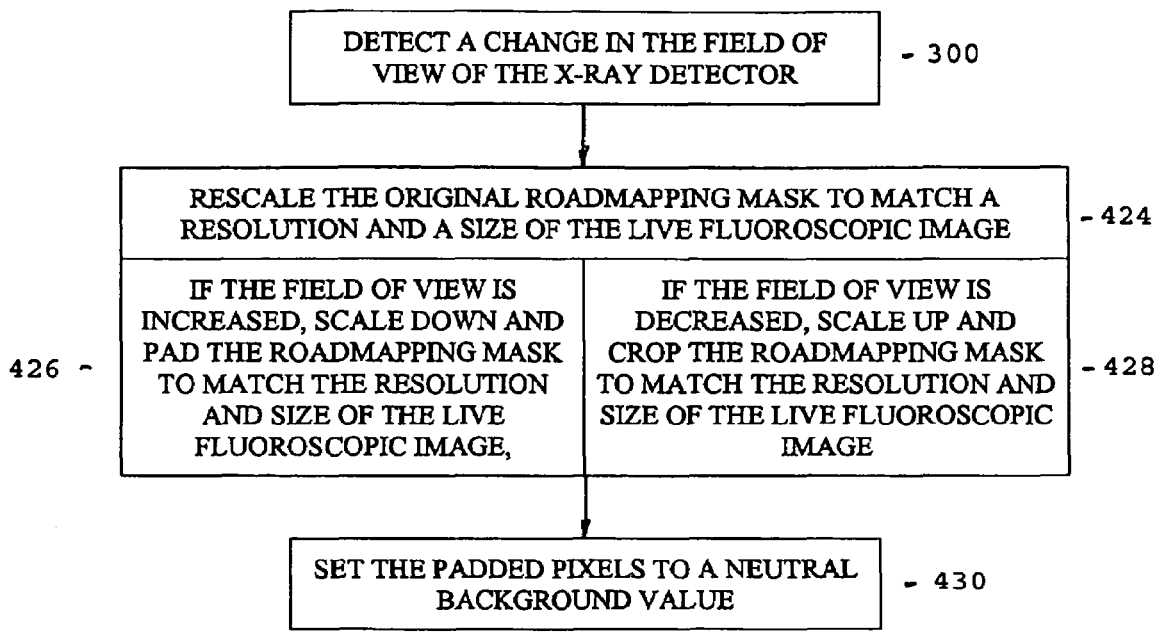

Depending on the nature of the parameter change detected at step 300: FIGS. 6B-6D describe the individual process steps that occur to accommodate the particular change. Thus, where the detected change (step 300) is determined to be a change in position of the patient table 6, a new field of view of the x-ray detector 24 is predicted based on that position change (step 410, FIG. 6B). The roadmapping mask is then panned (step 412) according to the predicted new field of view by translating the original roadmapping mask in the direction of table movement by an amount equal to the change in relative location between the table and the x-ray detector 24. Pixels that are undefined as a result of the translation step are then set to a neutral background value at step 414.

Where the detected change (step 300) is determined to be a change in distance between the x-ray source 2 and x-ray detector 24, then the original roadmapping mask is rescaled to match a pixel size of the live fluoroscopic image based on that detected change (step 416, FIG. 6C). If the detected change represents an increase in the distance between the source and detector, then the original roadmap mask is enlarged and cropped to match the size of the live fluoroscopic image (step 418). If the detected change represents a decrease in the distance between the source and detector, then the original roadmap mask is reduced and padded to match the size of the fluoroscopic image (step 420). Any pixels that are undefined as a result of the size change step are set to a neutral background value at step 422.

Where the detected change (step 300) is determined to be a change in the field of view of the x-ray detector 24, then the original roadmapping mask is rescaled at step 424 to match a resolution and size of the live fluoroscopic image. If the field of view is determined to have increased, then at step 426 the roadmapping mask is scaled down and the padded to match the resolution and size of the live fluoroscopic image. If the field of view is determined to have decreased, then at step 428 the roadmapping mask is scaled up and cropped to match the resolution and size of the live fluoroscopic image. Any pixels that are undefined as a result of the size change step are set to a neutral background value at step 430.

The method described herein may be automated by, for example, tangibly embodying a program of instructions upon a computer readable storage media capable of being read by machine capable of executing the instructions. A general purpose computer is one example of such a machine. A non-limiting exemplary list of appropriate storage media well known in the art would include such devices as a readable or writeable CD, flash memory chips (e.g., thumb drives), various magnetic storage media, and the like.

The features of the method have been disclosed, and further variations will be apparent to persons skilled in the art. All such variations are considered to be within the scope of the appended claims. Reference should be made to the appended claims, rather than the foregoing specification, as indicating the true scope of the disclosed method.

The functions and process steps herein may be performed automatically or wholly or partially in response to user command. An activity (including a step) performed automatically is performed in response to executable instruction or device operation without user direct initiation of the activity.

The systems and processes of FIGS. 1-6 are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. The processes and applications may, in alternative embodiments, be located on one or more (e.g., distributed) processing devices accessing a network linking the elements of FIG. 1. Further, any of the functions and steps provided in FIGS. 1-6 may be implemented in hardware, software or a combination of both and may reside on one or more processing devices located at any location of a network linking the elements of FIG. 1 or another linked network, including the Internet.

What is claimed is:

1. A method for adjusting an angiographic roadmapping mask, comprising:
   obtaining an original roadmapping mask of a targeted patient tissue region;
   obtaining a live fluoroscopic image of at least a portion of the targeted patient tissue region using an x-ray source and an x-ray detector;
   sensing a change comprising at least one of: a position change of a patient table, a change in a distance between the x-ray source and the x-ray detector, and a change in a field of view of the x-ray detector;
   adjusting the roadmapping mask to match the live fluoroscopic image in response to the sensed change; and
   combining the adjusted roadmapping mask and the live fluoroscopic image to provide a displayed superimposed image to a user.

2. The method of claim 1, wherein the step of adjusting the roadmapping mask comprises detecting a position change of a patient table, predicting a new field of view of the x-ray detector based on the detected position change, and panning the roadmapping mask according to predicted new field of view.

3. The method of claim 2, wherein the panning step comprises translating the original roadmapping mask in the direction of table movement by an amount equal to the change in relative location between the table and the detector.

4. The method of claim 3, further comprising setting any pixels that are undefined as a result of the translating step to a neutral background value to minimize subtraction artifacts in areas of the live fluoroscopic image for which no roadmapping mask was acquired.

5. The method of claim 1, wherein the step of adjusting the roadmapping mask comprises detecting a change in a distance between the x-ray source and the x-ray detector, and re-scaling the original roadmapping mask to match a pixel size of the live fluoroscopic image based on the detected change.

6. The method of claim 5, wherein when the detected change represents an increase the original roadmapping mask is enlarged and cropped to match the size of the live fluoroscopic image, and wherein when the detected change represents a decrease the original roadmapping mask is reduced and padded to match the size of the live fluoroscopic image.

7. The method of claim 6, wherein the padded pixels are set to a neutral background value to minimize subtraction artifacts in areas of the live fluoroscopic image for which no roadmapping mask was acquired.

8. The method of claim 1, wherein the step of adjusting the roadmapping mask comprises detecting a change in the field of view of the x-ray detector, and re-scaling the original roadmapping mask accordingly to match a resolution and a size of the live fluoroscopic image.

9. The method of claim 8, wherein when the field of view is increased the roadmap mask is scaled down and padded to match the resolution and size of the live fluoroscopic image, and when the filed of view is decreased the roadmapping mask is scaled up and cropped to match the resolution and the size of the live fluoroscopic image.

10. The method of claim 9, wherein the padded pixels are set to a neutral background value to minimize subtraction artifacts in areas of the live fluoroscopic image for which no roadmapping mask was acquired.

11. The method of claim 1, wherein the step of adjusting the roadmapping mask comprises:
sensing a movement of the patient table;
applying a conversion factor to the sensed movement of the patient table to obtain a pixel movement value for the original roadmapping mask, where the conversion factor is determined using the relative geometric positioning of the x-ray source, the x-ray detector, and the patient table; and
translating the original roadmapping mask by the pixel movement value.

12. The method of claim 1, wherein the step of adjusting the roadmapping mask comprises:
sensing a change in distance between the x-ray source and one of the patient table and the x-ray detector;
applying a conversion factor to convert the change in distance into a discrete change in pixel size of the original roadmapping mask, where the conversion factor is determined using a triangulation between the x-ray source, the x-ray detector, and the patient table; and
resizing the original roadmapping mask by the change in pixel size.

13. The method of claim 1, wherein the step of adjusting the roadmapping mask comprises:
determining an initial field of view of the x-ray detector and calculating a pixel size of the x-ray detector based on the initial field of view;
sensing a change in the initial field of view of the x-ray detector and converting the sensed change into a proportional change in the pixel size; and
changing the scale of the original roadmapping mask based on the proportional change in the pixel size.

14. The method of claim 1, wherein the combining step comprises digitally subtracting the adjusted roadmapping mask from the live fluoroscopic image.

15. A method for performing angiographic roadmapping, comprising:
obtaining an original roadmapping mask of a targeted patient tissue region using an x-ray source and an x-ray detector;
obtaining a live fluoroscopic image of at least a portion of the targeted patient tissue region;
sensing a change comprising at least one of: a position change of a patient table, a change in a distance between the x-ray source and the x-ray detector, and a change in a field of view of the x-ray detector;
adjusting the original roadmapping mask to match a portion of the live fluoroscopic image in response to the sensed change; and
combining the adjusted roadmapping mask and the live fluoroscopic image to provide a displayed superimposed image to a user.

16. The method of claim 15, wherein the step of adjusting the original roadmapping mask comprises detecting a position change of a patient table positioned adjacent to the x-ray detector, predicting a new field of view of the x-ray detector based on the detected position change, and panning the original roadmapping mask according to the predicted new field of view.

17. The method of claim 16, wherein the panning step comprises translating the original roadmapping mask by an amount equal to the change in relative location between the table and the detector.

18. The method of claim 17, further comprising setting any pixels that are undefined as a result of the translating step are set to a predetermined value to minimize subtraction artifacts in areas of the live fluoroscopic image for which no roadmapping mask was acquired.

19. The method of claim 15, wherein the step of adjusting the original roadmapping mask comprises detecting a change in a distance between the x-ray source and the x-ray detector, and re-scaling the original roadmapping mask to match a pixel size of the live fluoroscopic image based on the detected change.

20. The method of claim 19, wherein when the detected change represents an increase, the original roadmapping mask is enlarged and cropped to match the size of the live fluoroscopic image, and wherein when the detected change represents a decrease, the original roadmapping mask is reduced and padded to match the size of the live fluoroscopic image.

21. The method of claim 20, wherein the padded pixels are set to a predetermined value to minimize subtraction artifacts in areas of the live fluoroscopic image for which no roadmapping mask was acquired.

22. The method of claim 15, wherein the step of adjusting the original roadmapping mask comprises detecting a change in a field of view of the x-ray detector and re-scaling the original roadmapping mask accordingly to match a resolution and a size of the live fluoroscopic image.

23. The method of claim 22 wherein when the field of view is increased the roadmapping mask is scaled down and the image padded to match the resolution and size of the live fluoroscopic image, and when the field of view is decreased the roadmapping mask is scaled up and the image cropped to match the resolution and the size of the live fluoroscopic image.

24. The method of claim 23, wherein the padded pixels are set to a predetermined value to minimize subtraction artifacts in areas of the live fluoroscopic image for which no roadmapping mask was acquired.

25. The method of claim 15, wherein the step of adjusting the roadmapping mask comprises:
sensing a movement of the patient table;
applying a conversion factor to the sensed movement of the patient table to obtain a pixel movement value for the original roadmapping mask, where the conversion factor is determined using the relative geometric positioning of the x-ray source, the x-ray detector, and the patient table; and
translating the original roadmapping mask by the pixel movement value.

26. The method of claim 15, wherein the step of adjusting the roadmapping mask comprises:
sensing a change in distance between the x-ray source and one of the patient table and the x-ray detector;
applying a conversion factor to convert the change in distance into a discrete change in pixel size of the original roadmapping mask, where the conversion factor is determined using a triangulation between the x-ray source, the x-ray detector, and the patient table; and
resizing the original roadmapping mask by the change in pixel size.

27. The method of claim 15, wherein the step of adjusting the roadmapping mask comprises:
determining an initial field of view of the x-ray detector and calculating a pixel size of the x-ray detector based on the initial field of view;
sensing a change in the initial field of view of the x-ray detector and converting the sensed change into a proportional change in the pixel size; and changing the scale of the original roadmapping mask based on the proportional change in the pixel size.

28. The method of claim 15, wherein the combining step comprises digitally subtracting the adjusted roadmapping mask from the live fluoroscopic image.

29. A system for adjusting an angiographic roadmapping mask, comprising:
an x-ray source, an x-ray detector, a patient table, a display; and
a machine-readable storage medium encoded with a computer program code such that, when the computer program code is executed by a processor, the processor performs a method comprising:
obtaining an original roadmapping mask of a targeted patient tissue region;
obtaining a live fluoroscopic image of at least a portion of the targeted patient tissue region using the x-ray source and the x-ray detector;
sensing a change comprising at least one of: a position change of a patient table, a change in a distance between the x-ray source and the x-ray detector, and a change in a field of view of the x-ray detector;
adjusting the original roadmapping mask to match a portion of the live fluoroscopic image in response to the sensed change;
combining the adjusted roadmapping mask and the live fluoroscopic image to provide a superimposed image; and
displaying the superimposed image to a user via the display.

30. The system of claim 29, wherein method performed by the processor further comprises detecting a position change of a patient table, predicting a new field of view of the x-ray detector based on the detected position change, and panning the roadmapping mask according to predicted new field of view.

31. The system of claim 30, wherein panning the roadmapping mask comprises translating the original roadmapping mask in the direction of table movement by an amount equal to the change in relative location between the table and the detector.

32. The system of claim 31, wherein the method performed by the processor further comprises setting any pixels that are undefined as a result of translating step to a neutral background value to minimize subtraction artifacts in areas of the live fluoroscopic image for which no roadmapping mask was acquired.

33. The system of claim 29, wherein adjusting the roadmapping mask comprises detecting a change in a distance between the x-ray source and the x-ray detector, and re-scaling the original roadmapping mask to match a pixel size of the live fluoroscopic image based on the detected change.

34. The system of claim 33, wherein when the detected change represents an increase, the method performed by the processor further comprises enlarging and cropping the original roadmap mask to match the size of the live fluoroscopic image, and wherein when the detected change represents a decrease, the method performed by the processor further comprises reducing and padding the original roadmapping mask to match the size of the live fluoroscopic image.

35. The system of claim 34, wherein the method performed by the processor further comprises setting the padded pixels to a neutral background value to minimize subtraction artifacts in areas of the live fluoroscopic image for which no roadmapping mask was acquired.

36. The system of claim 29, wherein the step of adjusting the roadmapping mask comprises detecting a change in the field of view of the x-ray detector, and re-scaling the original roadmapping mask accordingly to match a resolution and a size of the live fluoroscopic image.

37. The system of claim 36, wherein when the field of view is increased, the method performed by the processor further comprises scaling down and padding the roadmapping mask to match the resolution and size of the live fluoroscopic image, and when the filed of view is decreased, the method performed by the processor further comprises scaling up and cropping the roadmapping mask to match the resolution and the size of the live fluoroscopic image.

38. The system of claim 35, wherein the padded pixels are set to a neutral background value to minimize subtraction artifacts in areas of the live fluoroscopic image for which no roadmapping mask was acquired.

39. The system of claim 29, wherein the step of adjusting the roadmapping mask comprises:
sensing a movement of the patient table;
applying a conversion factor to the sensed movement of the patient table to obtain a pixel movement value for the original roadmapping mask, where the conversion factor is determined using the relative geometric positioning of the x-ray source, the x-ray detector, and the patient table; and
translating the original roadmapping mask by the pixel movement value.

40. The system of claim 29, wherein the step of adjusting the roadmapping mask comprises:
sensing a change in distance between the x-ray source and one of the patient table and the x-ray detector;
applying a conversion factor to convert the change in distance into a discrete change in pixel size of the original roadmapping mask, where the conversion factor is determined using a triangulation between the x-ray source, the x-ray detector, and the patient table; and
resizing the original roadmapping mask by the change in pixel size.

41. The system of claim 29, wherein the step of adjusting the roadmapping mask comprises:
determining an initial field of view of the x-ray detector and calculating a pixel size of the x-ray detector based on the initial field of view;
sensing a change in the initial field of view of the x-ray detector and converting the sensed change into a proportional change in the pixel size; and
changing the scale of the original roadmapping mask based on the proportional change in the pixel size.

42. The system of claim 29, wherein the combining step comprises digitally subtracting the adjusted mask from the live fluoroscopic image.

* * * * *